United States Patent [19]
Bond, Jr. et al.

[11] 3,994,947
[45] Nov. 30, 1976

[54] FULVENE-SILANE ADDUCT AND ETHYLENE INTERPOLYMERS EMBODYING SAME

[75] Inventors: William C. Bond, Jr.; Harold J. Wahlborg, both of Baton Rouge, La.

[73] Assignee: Copolymer Rubber & Chemical Corporation, Baton Rouge, La.

[22] Filed: Feb. 10, 1975

[21] Appl. No.: 548,741

Related U.S. Application Data

[60] Division of Ser. No. 320,482, Jan. 2, 1973, abandoned, which is a continuation of Ser. No. 112,068, Feb. 2, 1971, abandoned.

[52] U.S. Cl. .................. 260/448.2 Q; 260/448.8 R; 526/279
[51] Int. Cl.² ...................... C07F 7/12; C07F 7/14; C07F 7/18

[58] Field of Search .............. 260/448.8 R; 260/448.2 Q

[56] References Cited
UNITED STATES PATENTS

| | | | |
|---|---|---|---|
| 2,697,089 | 12/1954 | Kleiman | 260/448.2 Q X |
| 3,290,359 | 12/1966 | Mark | 260/448.8 R X |
| 3,664,403 | 5/1972 | Doran et al. | 260/448.8 R X |
| 3,737,334 | 6/1973 | Doran et al. | 260/448.8 R X |

*Primary Examiner*—Paul F. Shaver
*Attorney, Agent, or Firm*—McDougall, Hersh & Scott

[57] ABSTRACT

An adduct of a fulvene and unsaturated silane produced in a Diels-Alder reaction and the interpolymerization of the adduct with ethylene, with or without propylene, with or without a polyene, in the preparation of ethylene interpolymers.

6 Claims, No Drawings

FULVENE-SILANE ADDUCT AND ETHYLENE INTERPOLYMERS EMBODYING SAME

This is a division of application Ser. No. 320,482, filed Jan. 2, 1973, which is a continuation of Ser. No. 112,068, filed Feb. 2, 1971, now abandoned.

This invention relates to the reaction products of fulvenes with unsaturated organo silicon compounds to produce a Diels-Alder adduct which can be utilized as a monomer in the manufacture of ethylene interpolymers, with ethylene as the first monomer and with or without a monoolefin having from 3–20 carbon atoms as the third monomer, or which can be used as the fourth monomer in the manufacture of EPDM tetrapolymers of ethylene, a monoolefin as previously described and a polyene to impart curability or vulcanizability with sulfur to the interpolymer that is formed, and it relates more particularly to the manufacture of such Diels-Alder adducts.

It is an object of this invention to produce and to provide a method of producing a compound having the general formula

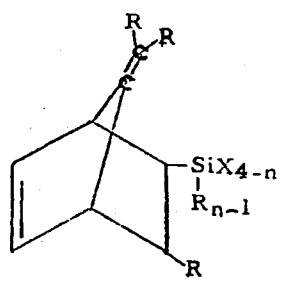

in which R may be hydrogen, a lower alkyl group, such as methyl, ethyl, propyl, isopropyl, butyl, pentyl and the like, a halogen substituted lower alkyl group and in which R may also be an unsaturated organic group such as vinyl, allyl, norbornenyl and the like, X is a highly hydrolyzable group such as a tertiary amino group, a halogen group such as chlorine, bromine, iodine and the like, and n is a number of from 1 to 3, and it is a related object of this invention to produce and to provide a method for producing the compound 7-isopropylidenyl-5-trichlorosilyl-2-norbornene.

It is another object of this invention to make use of a compound of the type described as a monomer in the preparation of interpolymers of ethylene, with or without one or more monoolefins containing from 3-20 carbon atoms with or without a polyene.

Referring first to the compounds of this invention, they may be prepared in accordance with the following equation:

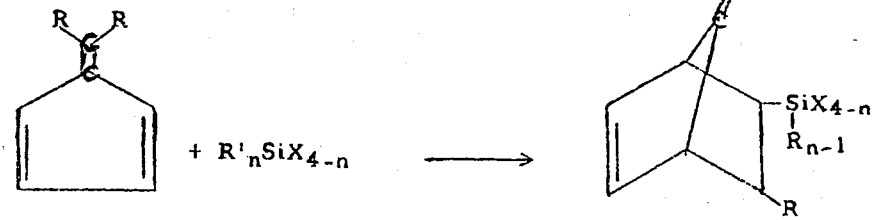

in which R and R' may be hydrogen, a lower alkyl group, such as methyl, ethyl, propyl, isopropyl, butyl, pentyl and the like, a halogen substituted lower alkyl group and in which R and R' may be an unsaturated organic group such as vinyl, allyl, norbornenyl and the like, but in which at least one R' group is an unsaturated group, X is a highly hydrolyzable group such as a tertiary amino group, a halogen group such as chlorine, bromine, iodine and the like, and $n$ is a number of from 1 to 3.

In the preferred practice of this invention, R is methyl, R' is vinyl, X is chlorine and n is 1, dimethyl fulvene is reacted with vinyltrichlorosilane to produce 7-isopropylidenyl-5-trichlorosilyl-2-norbornene, as represented by the following equation:

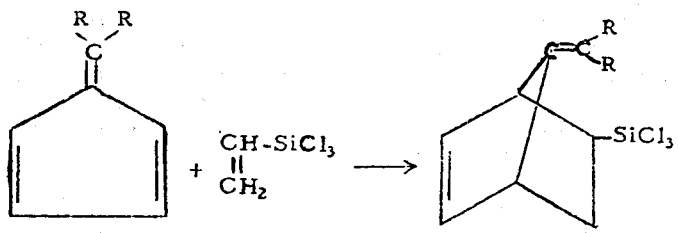

The reaction is carried out preferably in solution in an inert organic solvent such as benzene, toluene and the like, with the reactants present in the stoichiometric amounts plus or minus 50% by weight, with the more available and more easily separable component present in excess to drive the reaction to the right.

The following examples are given by way of illustration, but not by way of limitation, of the preparation of compounds of this invention:

EXAMPLE 1

Into a dry, nitrogen flushed, three-necked, 100 ml flask equipped with a thermometer, condenser, addition funnel and magnetic stirrer, addition was made of 40 g of vinyltrichlorosilane and 23.5 g of dimethylfulvene. The mixture was heated to reflux and the temperature then slowly rose to 90° C and was maintained for one-half hour. The HCl was removed by means of a water aspirator and then the reaction mixture was distilled. A single cut of pale yellow liquid (7.3 g) was recovered at 75° C and 0.4 mm of mercury and identified by Nuclear Magnetic Resonance to be 7-isopropylidenyl-5-trichlorosilyl-2-norbornene. The NMR spectrum displayed definitive bands at $\delta = 1.52$ (sharp singlet; allylic methyls), $\delta = 3.44$ (broad; diallylic bridgehead protons), and $\delta = 6.20$ (broad singlet; olefinic norbornene ring protons). A chemical chlorine 37.90%, and silicon 10.19%. The calculated values are as follows: C, 45.15%; H, 4.89%; Cl, 39.66%; Si, 10.56%.

Into the flask similar to that used in Example 1, addition was made of 48 g vinyltrichlorosilane, 21.5 g of dimethylfulvene, and 15 ml of anhydrous benzene. On the addition of the dimethylfulvene there was a slight exotherm. The reaction was carried out with stirring at room temperature for one-half hour and then heated to reflux. Reflux started at 78° C and then slowly climbed to 100° C. After three hours at reflux, the reaction was cooled to room temperature. The product was distilled by stripping off benzene and unreacted starting material and recovering the product by distillation within the range of 70°–71° C and 0.4 mm mercury. A yield of 20 g (37.7% of theoretical) of 7-isopropylidenyl-5-trichlorosilyl-2-norbornene was obtained.

The reaction proceeds with the formation of a relatively large amount of undesirable polymeric residue. It has been found that the formation of polymeric residue can be greatly reduced and the yield markedly increased by the presence in the reaction mixture of a small amount of a hydrogen halide scavenger, for example a tertiary amine such as pyridine and the like and preferably collidene or other substituted pyridines. The tertiary amine, or other hydrogen halide scavenger which can be added with the dimethylfulvene, not only operates to improve the yield of the product and reduce polymer formation, but it also conserves the starting material to enable re-use or recycle thereby greatly to increase the efficiency of the reaction. It is sufficient if the hydrogen halide scavenger is present in the reaction mixture in an amount within the range of 0.1 to 10% and preferably 2 to 5% by weight of the reactants.

The following will illustrate the further improvement in the process and product of this invention:

EXAMPLE 2

A 250 ml pressure bottle was charged with 25 ml benzene, 47.5 g dimethylfulvene, 4.5 g collidene and 108 g vinyltrichlorosilane. The bottle was purged with nitrogen, sealed and heated to 125° C for 3 hours. The reaction mixture was cooled, filtered and distilled. Starting material was recovered and 63.6 g of product boiling at 97°–100° C at 2 mm mercury was obtained with only 7 g of residue. The yield of 7-isopropylidenyl-5-trichlorosilyl-2-norbornene was 53%.

Instead of collidene, pyridine, other tertiary amines or hydrogen halide scavengers can be used in Example 2.

EXAMPLE 3

A 250 ml pressure bottle was charged and treated as in Example 3 except that an additional 25 ml of benzene and no hydrogen halide scavenger were present. There appeared to be some polymerization when all the reactants were combined. Some starting material was recovered, 25.3 g of product was distilled and 36 g of high boiling residue was left in the pot. The yield of 7-isopropylidenyl-5-trichlorosilyl-2-norbornene amounted to 20.8% of theoretical.

The compounds of this invention are characterized by a number of reactive sites: For example an internal double bond which is highly polymerization active by reason of the strained ring and "ylidenyl" type linkages; the isopropylidenyl group that remains after polymerization has six allylic hydrogens on the methyl groups attached to the strained double bond which renders the compound reactive for cure or vulcanization; and the highly hydrolyzable groups, such as the halogen groups, which remain attached to the silicon atom which, when incorporated into a polymer, give active sites for further reaction such as branching, crosslinking, substitution, grafting and the like. By reason of these novel functions, the compounds of this invention can be used to advantage as a monomer in the preparation of curable or sulfur vulcanizable interpolymers by interpolymerization with ethylene with or without at least one monoolefin having from 3–20 carbon atoms, preferably propylene, or as a fourth monomer in the preparation of curable or sulfur vulcanizable interpolymer by reaction with ethylene, at least one monoolefin having from 3–20 carbon atoms, preferably propylene, and a polyene, in the normal manner for the preparation of EPDM rubbers.

The novel interpolymers of the invention are prepared by interpolymerizing a monomeric mixture containing ethylene, the monomer produced in accordance with the practice of this invention, and with or without one or more alpha-monoolefins containing 3–20 carbon atoms and preferably 3–10 carbon atoms, and with or without a polyene, in solution in an inert organic solvent and in the present of a Ziegler type catalyst to be described more fully hereinafter.

In the practice of this invention, it is preferred that the interpolymer of ethylene with the monomer of this invention are chemically bound between the weight ratios of ethulene to monomer of 99.95 to 0.05 and 80.0 to 20.0 and preferably between 99.9 to 0.10 and 90.0 to 10.0.

In the practice of this invention it is preferred that the interpolymers be prepared from a monomeric mixture in which the ethylene and straight chain higher monoolefin, such as propylene, are chemically bound in the molecular ratios of ethylene to propylene varying between 90:5 and 10:90 and preferably between 70:30 and 55:45.

The monomer of this invention and the polyene, when employed in a tetrapolymer, are chemically bound in the elastomer in an amount to provide an effective unsaturation level of at least 1.5 and preferably at least 2 carbon-to-carbon double bonds per 1000 carbon atoms in the polymer. Much higher effective unsaturation levels are possible such as up to 50 or more carbon-to-carbon double bonds per 1000 carbon atoms. The specific effective unsaturation level which is selected in a given instance will vary depending upon the properties desired in the elastomer.

The polymerization solvent may be any suitable organic solvent which is liquid and inert under the reaction conditions, and it may be a prior art solvent for solution polymerization of monoolefins in the presence of Ziegler catalysts. Examples of satisfactory hydrocarbon solvents include acyclic paraffins and olefins containing 3–8 carbon atoms, of which hexane often is preferred; aromatic hydrocarbons and especially those containing a single benzene nucleus such as benzene, toluene, etc.; and saturated cyclic hydrocarbons which have boiling ranges approximating those for the straight chain paraffin hydrocarbons and aromatic hydrocarbons discussed above, and especially saturated cyclic hydrocarbons containing 5 or 6 carbon atoms in the ring, or chlorinated hydrocarbons such as carbontetrachloride, chlorobenzene and tetrachloroethylene. The solvent selected may be a mixture of one or more of the foregoing, such as a mixture of aliphatic and naphthenic hydrocarbon isomers having approximately the same boiling range as normal benzene. It is necessary that the solvent be dry and free of substances which will interfere with the catalyst to be used in the polymerization step.

Ziegler catalysts in accordance with the prior art may be used. In general, any suitable prior art Ziegler-type catalyst may be used which is known to produce a satisfactory elastomer. Ziegler catalysts are disclosed in a large number of issued patents, such as U.S. Pat. Nos. 2,933,480, 3,093,620, 3,093,621, 3,211,709 and 3,113,115. Examples of Ziegler catalysts include metal organic coordination catalysts prepared by contacting a compound of a heavy catalyst metal of Groups IVb, Vb, VIb and VIIb of the Mendelejeff periodic chart of the elements, as typified by titanium, vanadium and chromium halides with an organometallic compound of a metal of Groups I, II and II of the Mendelejeff periodic chart which contains at least one carbon-metal bond, as typified by trialkyl aluminum and alkyl aluminum halides wherein the alkyl groups contain 1–20 and preferably 1–4 carbon atoms. The term Ziegler catalyst as used herein is intended to embrace catalysts of the foregoing types, some of which are often referred to as Ziegler-Natta or low pressure polymerization catalysts for alpha-monoolefins.

The preferred Ziegler catalyst for many polymerizations is prepared from a vanadium compound and an alkyl aluminum halide. Examples of suitable vanadium compounds include vanadium trichloride, vanadium tetrachloride, vanadium oxychloride, vanadium acetylacetonate, etc. Activators which are especially preferred include alkyl aluminum chlorides of the general formulae $R_1AlCl_2$ and $R_2AlCl$, and the corresponding sesquichlorides of the general formula $R_3Al_2Cl_3$, wherein R is a methyl, ethyl, propyl, butyl or isobutyl radical. In the catalytic system, the aluminum to vanadium mole ratio of the aluminum and vanadium compounds may be within the range of 5:1 to 200:1 and preferably within the range of 10:1 to 60:1. These same ratios apply with respect to the corresponding compounds of heavy metals of the Groups IVb, Vb, VIb and VIIb for the vanadium compound and the organometallic compounds of Groups I, II or III for the aluminum compound. A catalyst prepared from alkyl aluminum sesquichloride, such as the methyl or ethyl aluminum sesquichloride and vanadium oxychloride is especially preferred and, when using this catalyst, the preferred ratio of catalyst components is usually 1 mole vanadium oxychloride for each 5–200 moles of aluminum and, more preferably, for each 10–60 moles of aluminum.

The polyene or other ethylenically unsaturated compound containing a plurality of carbon-to-carbon double bonds may be selected from those disclosed in the prior art, including open chain polyunsaturated hydrocarbons containing 4-°carbon atoms such as 1,4-hexadiene, monocyclic polyenes, and polycyclic polyenes. The polyunsaturated bridged-ring hydrocarbons or halogenated bridged-ring hydrocarbons are usually preferred. Examples of the bridged-ring hydrocarbons include the polyunsaturated derivatives of bicyclo(2,2,1)heptane wherein at least one double bond is present in one of the bridged rings, such as dicyclopentadiene, bicyclo(2,2,1)hepta-2,5-diene, the alkylidene norbornenes, and especially the 5-alkylidene-2-norbornenes wherein the alkylidene group contains 1–20 carbon atoms and preferably 1–8 carbon atoms, the alkenyl norbornenes, and especially the 5-alkenyl-2-norbornenes wherein the alkenyl group contains about 2-20 carbon atoms and preferably 3–10 carbon atoms. Other bridged-ring hydrocarbons include polyunsaturated derivatives of bicyclo(2,2,2)octane as represented by bicyclo(2,2,2)octa-2,5-diene, polyunsaturated derivatives of bicyclo(3,2,1)octane, polyunsaturated derivatives of bicyclo(3,3,1)nonane, and polyunsaturated derivatives of bicyclo(3,3,2)nonane. At least one double bond is present in a bridged ring of the above compounds, and at least one other double bond is present in a bridged ring or in a side chain. Further examples of polyunsaturated bridged-ring hydrocarbons and their use in the preparation of prior art elastomers are found in U.S. Pat. Nos. 2,933,480, 3,093,620, 3,093,621 and 3,211,709, the disclosures of which are incorporated hereby by reference.

Specific examples of preferred bridged-ring compounds include 5-methylene-2-norbornene, 5-ethylidene-2-norbornene, 5-n-propylidene-2-norbornene, 5-isopropylidene-2-norbornene, 5-n-butylidene-2-norbornene, 5-isobutylidene-2-norbornene, dicyclopentadiene, the methyl butenyl norbornenes such as 5-(2-methyl-2-butenyl)-2-norbornene or 5-(3-methyl-2-butenyl)-2-norbornene, and 5-(3,5-dimethyl-4-hexenyl)-2-norbornene.

The polymerization is preferably carried out on a continuous basis in a dry prior art reaction vessel closed to the outside atmosphere, which is provided with an agitator, reactor cooling means, and conduit means for continuously supplying the ingredients of the reaction mixture including monomers and catalyst, and conduit means for continuously withdrawing the solution of elastomer. The polymerization is carried out in liquid phase in the organic solvent and in the presence of the Ziegler catalyst. The solution of elastomer in the polymerization solvent is withdrawn continuously from the reaction vessel, the catalyst is killed by addition of a catalyst deactivator such as methanol or water, and the organic solvent is removed. The solvent may be removed by injecting the solution below the liquid level of a body of boiling water maintained in a vessel to which steam is supplied. The resulting polymer crumb is removed as a slurry from the vessel, and the polymerization solvent is withdrawn overhead as a vapor. The polymer crumb may be stripped free of traces of solvent and washed free of catalyst residues, followed by separating water from the crumb by means of a shaker screen or other device, and drying of the crumb by means of a prior art extrusion dryer or apron dryer. The dried crumb is then ready for baling in accordance with prior art practice.

The polyunsaturated organo silane, prepared in accordance with the practice of this invention, is employed in the monomer mixture in an amount within the range of 0.05 to 20% by weight of the monomer total and preferably in an amount within the range of 0.1 to 10.0% by weight.

For the interpolymerization reaction of the type described, it is desirable to make use of an adduct of this invention in which the highly hydrolyzable group attached to the silicon atom is other than an alkoxy group or other oxygen containing group, since such oxygen containing groups tend to kill the Ziegler type catalyst and destroy the reactivity required for interpolymerization.

The interpolymers of the invention may be cured following prior art procedures. As a general rule, a curing procedure which is normally followed in curing unsaturated hydrocarbon polymers, such as butyl rubber, styrene-butadiene rubber, natural rubber, polybutadiene rubber, polyisoprene rubbers, etc. is satisfactory.

Various curing procedures, including the materials and the quantities thereof to be employed, are described in a large number of publications which are well known in the art. These publications include "Principals of High Polymer Theory and Practice", Schmidt et al., McGraw-Hill Book Company, New York (1948); "Chemistry and Technology of Rubber", Davis et al., Reinhold Publishing Corporation, New York (1937); "The Applied Science of Rubber", edited by W. J. S. Naunton, published by Edward Arnold, Ltd., London (1961). "The Encyclopedia of Chemical Technology", Kirk and Othmer, published by Innerscience Encyclopedia, Inc., New York (1953), and "Compounding Ingredients for Rubbers", 3rd edition, Cuneo Press of New England, Cambridge, Mass.

As is taught by the above-mentioned texts, rubbery polymers may be vulcanized with vulcanizing agents including, for example, sulfur or sulfur bearing compounds which provide sulfur under the vulcanizing conditions. Sulfur is the preferred vulcanizing agent, and it is usually used in an amount of about 0.5 to 3, preferably about 1 to 2, parts by weight per hundred parts by weight of rubber in the blend. Zinc oxide and other metal oxides may be used in an amount of, for example, about 2 to 10 parts by weight per 100 parts by weight of rubber (phr). Vulcanization accelerators such as tetramethylthiuram monosulfide, tetramethylthiuram disulfide, the zinc salt of dimethyl dithiocarbamic acid, N,N-diethylthiocarbamyl-2-mercaptobenzothiazole and 2-mercaptozoline may be used, Conventional fillers and pigments may be incorporated with the polymer, such as about 100–400 phr of carbon black, finely divided silica, esterified silica, titanium dioxide, kaolin and whiting. It is also possible to oil extend the polymers. Naphthenic oils for use in processing or extending rubbery polymers are preferred, and are usually added in an amount of about 10–300 phr and preferably about 20–100 phr. Other types of oil may be used, such as the aromatic, highly aromatic and paraffinic oils.

However, it is a unique facet of this interpolymer that a great improvement over conventional EPDM polymers in physical properties such as tensile, modulus, compression set, tear resistance, and aging takes place when the interpolymer curing formulation contains certain fillers. The preferred fillers are similar in that they contain functional groups which have active hydrogens, such as hydroxyl, carboxyl, primary and secondary amino and sulfhydryl. Typical fillers are hard clay, soft clay, Silene-D, Hi Sil-233, Zeolex-23, Silene EF and the like. These preferred fillers can be used separately or in combination with each other or in combination with other fillers such as carbon black and other non-polar materials. The preferred fillers may also be used in combination with plasticizers and extender oils such as Shellflex 371-N, Circosol-4240 and the like.

Vulcanization is accomplished by heating the compounded polymers described above at a vulcanizing temperature and for a period of time sufficient for the vulcanization reaction to occur. A temperature of about 130°–180° C for about 10–90 minutes, and preferably about 160° C for about 30 minutes, is often satisfactory. The specific time and temperature that are selected in a given instance will depend upon the nature of the vulcanizing agent, accelerator, and other ingredients which are present.

When carrying out a free radical cure, a heat activated free radical curing agent is admixed with the polymer, and then the mixture is heated to a sufficiently elevated temperature to activate the curing agent and obtain a cure over a practical period of time. Usually, temperatures of about 50°–175° C for a period of 30 minutes to several hours is sufficient. Preferred free radical curing agents are organic peroxides such as dicumyl hydroperoxide, dibenzoyl peroxide, cumene hydroperoxide, ditertiarybutyl peroxide, and bis(alpha, alpha-dimethyl benzyl) peroxide.

The cured polymers of the invention may be used in a wide variety of articles, including tires, belts, hose, tubing, wire coatings, bottles, etc. For some reason that is not fully understood at the present time, the interpolymers of the invention have a much more rapid cure rate when cured with sulfur than would be predicted from the actual or theoretical carbon-to-carbon double bond content.

EXAMPLE 4

A dry flask flushed with nitrogen gas and containing 100 cc of dry hexane was fitted with a self-sealing cap. The hexane was flushed with polymerization grade propylene and then pressured to 15 p.s.i. with propylene. The flask was brought to 35 pounds total monomer pressure by addition from a feed tank containing 65 mole percent and 35 mole percent propylene. The polymerization was performed in a 35° C water bath shaker.

Additions were made of 0.03 mM of butyl perchlorocrotonate, 0.06 mM of pyridine, 0.6 mM of the adduct of dimethylfulvene and vinyltrichlorosilane from Examples 1 to 4, 9.6 mM of ethylaluminum sesquichloride and 0.0075 mM of vanadium oxytrichloride. As the polymerization proceeded, the monomer composition was maintained constant by continuous addition from the feed tank. At 300 seconds and again at 600 seconds, the above reactants were charged in the following amounts: 0.03 mM butyl perchlorocrotonate, 0.04 mM pyridine, 0.3 mM dimethylfulvene - vinyltrichlorosilane adduct, 0.3 mM ethylaluminum sesquichloride, 0.005 mM vanadium oxytrichloride, At 900 seconds, 0.4 cc of pyridine and 4 cc of methanol were added. After shaking for 1 hour, 0.05 g of Irganox 1010 was added.

The flask was vented and the contents blended with water. After coagulating the cement with isopropanol, the polymer was redissolved in hexane, recoagulated and dried in a vacuum oven at 80° C. An elastomer yield of 3.4 g was obtained having a spectrum with strong bands at 9.2 and 12.4 microns, indicating a high degree of incorporation of the adduct into the interpolymer.

EXAMPLE 5

This example illustrates the preparation of EPDM interpolymer which includes a polyene as the fourth monomer to impart curability and sulfur vulcanizability to the polymer.

A dry flask was first flushed with nitrogen gas and filled with 100 cc of dry hexane which was flushed with polymerization grade propylene and pressured to 15 p.s.i. with propylene. The flask was brought to 25 p.s.i.g. total pressure by addition from a feed tank containing 65 mole percent ethylene and 35 mole percent propylene. Polymerization was carried out in a water bath maintained at 35° C. Addition was made to the flask of the following reactants: 0.4 mM 5-ethylidene-2-norbornene, 0.3 mM of the adduct of dimethylfulvene and vinyltrichlorosilane, 0.03 mM butyl perchlorocrotonate, 0.04 mM pyridine, 0.3 mM ethylaluminum sesquichloride and 0.0075 mM vanadium oxytrichloride.

As the polymerization proceeded, the monomer composition in ethylene and propylene was maintained constant by continuous additions from the feed tank. At 300 seconds and again at 600 seconds, the above reactants were again charged to the flask and at 900 seconds, 0.3 cc of pyridine and 4 cc of methanol were added. After shaking for one hour, 0.05 g of Irganox 1010 was added. The flask was vented, the cement was coagulated with isopropanol, the polymer was redissolved in hexane, re-coagulated and dried.

The following are examples of continuous polymerization of procedures for producing interpolymers of this invention:

EXAMPLE 6

The reaction vessel was a one gallon Sutherland reactor equipped with a high speed, heavy-duty, air driven motor; cooling coils; a thermometer; a temperature regulator; a pressure regulator; an injection port; and other openings where monomers, catalyst, and solvent were fed to the reactor. A tube dipping to the bottom of the reactor was present for the removal of the cement produced on a continuous basis. A vapor phase vent was provided to bleed off 10% of the gaseous monomer feed to prevent inert gas buildup.

The clean reactor was assembled, rinsed with dry hexane and purged overnight with dry nitrogen. In the morning the reactor bowl was heated with a flameless blowtorch and hot water was run through the coils until the temperature in the reactor was about 70° C. After this, propylene was flushed through the reactor for about 15 minutes; then the temperature was lowered to ambient and 2 liters of Esso chemical grade hexane, dried over 4A molecular sieves, and silica gel, and stored over sodium, was added to the reactor. As the temperature was brought to 43° C propylene was fed to the reactor through a 4A molecular sieve column until 5.75 feet HG pressure was reached. The pressure was then brought up to 30 p.s.i.g. with ethylene fed through a 4A molecular sieve column and 0.96 cc of 4.3 mM of isopropylidene-5-trichlorosilyl-2-norbornene and 2.6 cc of 1.5 M ethylaluminum sesquichloride were added.

The monomers were shut off and the catalysts, 0.30 molar ethylaluminum sesquichloride and 0.009 molar vanadium oxytrichloride and 0.63 molar butylperchlorocrotonate at a 40/1/7 aluminum to vanadium to promoter ratio, were fed into the reactor at a constant rate until a drop in pressure in the reactor was noted. At this time the gaseous monomers were fed into the reactor through suitably calibrated rotometers at a rate of 3238 cc/minute, of which 1824 cc were ethylene and 1414 cc were propylene; the 7-isopropylidenyl-5-trichlorosilyl-2-norbornene was added as a 0.476 M solution in hexane at 1.72 cc/minute which provided about 5.7 weight percent to be incorporated into the polymer. The polymerization was controlled by the catalyst pumps which added catalyst on demand as the pressure increased, thus maintaining the 30 pounds pressure throughout the run. When the solution became approximately 8 weight percent polymer, solvent containing 16 cc/cc ethylene was fed at the rate of 55.8 cc per minute into the reactor and the polymer cement taken off which produced about 230 g of polymer per hour.

At this time the ethylene and propylene feeds were adjusted to 987 cc/minute and 2885 cc/minute to compensate for the unreacted monomers removed with the cement.

The solution cement as removed from the reactor was fed to a second stirred vessel which contained anhydrous methanol, then after waiting 30 minutes the cement was washed three times with equal volumes of water in a separatory funnel. The washed and stabilized cement containing 0.1 part Irganox 1010 was fed with nitrogen pressure into a tee joint at the bottom of a 4-liter container full of hot circulating water. The other end of the tee is connected to a steam line and steam was admitted at such a rate as to superheat the rubber cement. The solvent and reacted monomers were mostly removed by this procedure. The rubber crumb was collected on a screen, washed and chopped up in a Waring Blendor. The rubber crumb was dried in the oven at 90° C to remove any remaining solvent and water giving a rubbery copolymer which contained 63 mole percent ethylene by infrared analysis, using the 720 $cm^{-1}$ absorbance for ethylene and the 968 $cm^{-1}$ absorbance for propylene. The unsaturation expressed in C=C/1000 carbon atoms was about 2.8.

The polymer was analyzed for unsaturation by the consumption of bromine correcting for the substitution reaction by a differential kinetic method based on the spectrophotometric method developed by Siggia et al., Anal. Chem. 35, 362 (1963). Curing of the dried rubber was effected by compounding in a Brabender plasticorder (or Banbury size B mixer) based on 100 parts of rubber, 40 parts SRF, 40 parts HAF carbon black, 46 parts of a naphthenic rubber processing oil, 3 parts of zinc oxide, 0.75 parts Captex, 1.5 parts urads and 1.5 parts sulfur. Curing was for 15 minutes at 150° C. The cured properties as determined by standard ASTM methods D412-62T, D927-47, and D395-61-B are reported below.

The hardness was determined on a Shore A durometer. The belt life is the time in hours necessary for a 0.032° cut in a belt to grow to five times its original size when it is run on small pulleys in a chamber at 71° C. Heat rise ($\Delta T°$ F) is by the Goodrich method. The slope of the cure curve was determined on a Monsanto rheometer.

| Formulation | EPsyn 70/40 | Example 6 |
|---|---|---|
| Polymer | 50/50 | 105.5* |
| Crude $ML_{1+8}$ (250° F) | 55 | 48* |
| Compound $ML_{1+4}$ (212° F) | 70 | 100 |
| Tensile, psi | 2075 | 1150 |
| Elongation, % | 500 | 230 |
| 200% Modulus, psi | 675 | 1000 |

-continued

| Formulation | EPsyn 70/40 | Example 6 |
|---|---|---|
| Hardness, Shore A | 66 | 67 |
| Compression Set, % | | |
| 22 Hrs. at 158° F | 26.1 | 20.4 |
| Compound Green Tensile, psi | 63 | 69 |
| Compound Green Elongation, % | 175 | 175 |

*This includes 5.5 parts oil.

EXAMPLE 7

The reaction vessel was a one gallon Sutherland reactor equipped with a high speed, heavy duty, air driven motor; cooling coils; a thermometer; a temperature regulator; a pressure regulator; an injection port; and other openings where monomers, catalyst, and solvent were fed to the reactor. A tube dipping to the bottom of the reactor was present for the removal of the cement produced on a continuous basis. A vapor phase vent was provided to bleed off 10% of the gaseous monomer feed to prevent inert gas buildup.

The clean reactor was assembled, rinsed with dry hexane and purged overnight with dry nitrogen. In the morning the reactor bowl was heated with a flameless blowtorch and hot water was run through the coils until the temperature in the reactor was about 70° C. After this, propylene was flushed through the reactor for about 15 minutes; then the temperature was lowered to ambient and 2 liters of Esso chemical grade hexane, dried over 4A molecular sieves and stored over sodium, was added to the reactor. As the temperature was brought to 43° C propylene was fed to the reactor through a 4A molecular sieve column until 5.75 feet Hg pressure was reached. The pressure was then brought up to 30 pounds with ethylene fed through a 4A molecular sieve column and 0.62 cc or 2.8 mM 7-isopropylidene-5-trichlorosilyl-2-norbornene and 2.6 cc of 1.5 M ethylaluminum sesquichloride were added.

The monomers were shut off and the catalysts, 0.26 molar ethylaluminum sesquichloride, 0.008 molar vanadium oxytrichloride and 0.55 molar butylperchlorocrotonate at a 40/1/7 aluminum to vanadium to promoter ratio, were fed into the reactor at a constant rate until a drop in pressure in the reactor was noted. At this time the gaseous monomers were fed into the reactor through suitably calibrated rotometers at a rate of 3239 cc/minute, of which 1824 cc were ethylene and 1415 cc were propylene; the 7-isopropylidene-5-trichlorosilyl-2-norbornene was added as a 0.31 M solution in hexane at 1.72 cc/minute which provided about 3.8 weight percent to be incorporated into the polymer. The polymerization was controlled by the catalyst pumps which added catalyst on demand as the pressure increased, thus maintaining the 30 pounds HG pressure throughout the run. When the solution became approximately 8 weight percent polymer, solvent containing 16 cc/cc ethylene was fed at the rate of 54.6 cc per minute into the reactor and the polymer cement taken off which produced about 225 g of polymer per hour.

At this time the ethylene and propylene feeds were adjusted to 1015 cc/minute and 2853 cc/minute to compensate for the unreacted monomers removed with the cement.

The solution cement is removed from the reactor was fed to a second stirred vessel which contained anhydrous methanol, then after waiting 30 minutes the cement was washed three times with equal volumes of water in a separatory funnel. The washed and stabilized silane containing cement containing 0.1 part Irganox 1010 was fed with nitrogen pressure into a tee joint at the bottom of a 4-liter container full of hot circulating water. The other end of the tee is connected to a steam line and steam was admitted at such a rate as to superheat the ruber cement. The solvent and unreacted monomers were mostly removed by this procedure. The rubber crumb was collected on a screen, washed and chopped up in a Waring Blendor. The rubber crumb was fired in the oven at 90° C to remove any remaining solvent and water giving a rubbery copolymer which contained 63 mole percent ethylene by infrared analysis, using the 720 $cm^{-1}$ absorbance for ethylene and the 968 $cm^{-1}$ absorbance for propylene, and had a reduced specific viscosity in Decalin at 315° C of 2.16. The unsaturation expressed in C=C/1000 carbon atoms was 1.4.

The polymer was analyzed for unsaturation by the consumption of bromine correcting for the substitution reaction by a differential kinetic method based on the spectrophotometric method developed by Siggia et al., Anal. Chem. 35, 362 (1963). Curing of the dried rubber was effected by compounding in a Brabender plasticorder (or Banbury size B mixer) based on 100 parts of rubber, 40 parts SRF and 40 parts of HAF carbon black, 40 parts of a naphthenic rubber processing oil, 3 parts of zinc oxide, 1 part of stearic acid, 0.75 parts of mercaptobenzothiazole, 1.5 parts of tetramethylthiuram sulfide urads and 1.5 parts sulfur. Curing was for 15 minutes at 150° C. The cured properties as determined by standard ASTM methods D412-62T, D927-47, and D395-61-B are reported below.

The hardness was determined on a Shore A durometer. Heat rise ($\Delta T°$ F) is by the Goodrich method. The slope of the cure curve was determined on a Monsanto rheometer.

| Formulation | EPsyn 70 | Example 7 |
|---|---|---|
| Polymer | 100 | |
| Compound $ML_1$ (212° F) | 78 | 90 |
| Tensile, psi | 1925 | 1500 |
| Elongation, % | 430 | 340 |
| 300% Modulus, psi | 1350 | 1325 |
| Goodrich T | 47 | 49 |
| Compression Set, % | | |
| 22 Hrs. at 158° F | 23.7 | 15.6 |
| Compound Green Tensile, psi | 31 | 36 |
| Compound Green Elongation, % | 170 | 110 |
| Rheometer Cure rate | | |
| Units/min | 17.0 | 6.0 |
| T-90, min | 15.0 | 22.25 |
| Min. Torque, In/Lbs | 35 | 36 |
| Max. Torque, In/Lbs | 93 | 113 |
| T-S2, min.* | 2.5 | 1.5 |

*Scorch, Minutes to 2 inch lb. above minimum torque.

As described in our copending application entitled "EPDM Interpolymers formed with unsaturated organo silanes", filed on or about Dec. 31, 1970, the organo silicon, now present as a component of the formed interpolymer, provides an interpolymer which has a number of unique and interesting features.

By reason of the presence of the highly hydrolyzable groups attached to the silicon atom in the interpolymer, the formed interpolymer can be made to jump in molecular weight by crosslinking in response to the addition of water. Such water may be added to kill the catalyst with the removal of hydrolyzable groups to form the corresponding polymeric silanols which immediately react by condensation for crosslinking to increase the molecular weight, as described in Example 4. When water is added after the catalyst has been killed to stop the polymerization reaction but before the hydrolyzable groups have been removed, the described crosslinking with increase in molecular weight can still occur.

As further described in the aforementioned copending application, the interpolymer can be modified in various ways by reaction to replace hydrolyzable groups attached to the silicon atom, with alcohols, carboxylic acids, organic anhydrides, amines, phenols and the like to substitute such groupings for the halogen or other hydrolyzable group on the silicon atom. When the alcohol is a primary alcohol, such as methanol, ethanol, propanol, the OR group of the alcohol will substitute for the hydrolyzable group attached to the silicon atom to become a part of the interpolymer. By proper selection of the organic group of the alcohol, various modifications can be achieved. For example, when the organic group is an unsaturated group, such as in allyl alcohol, crotyl alcohol and the like, or when such group is an unsaturated group as a norbornenyl group, additional unsaturation can be incorporated into the interpolymer to enhance cure, crosslinking or the like.

When the alcohol is a secondary or tertiary alcohol such as isopropanol, sec-butanol, t-butanol and the like, the alcohol serves to kill the catalyst, as in Example 5, but without complete replacement of hydrolyzable groups attached to the silicon atom so that they will remain in the interpolymer for subsequent reaction, or for replacement with a primary alcohol, primary amine, carboxylic acid or anhydride and the like.

The groups which are substituted for the hydrolyzable group can take many forms. If the group is an anti-oxidant, as in an alcoholic or phenolic substitute anti-oxidant, the anti-oxidant will become part of the interpolymer to improve its oxidation resistance. If the group contains halogen, such as chlorine or bromine, such as 1,2,3,4,7,7-hexachloronorbornene-2-methanol, the interpolymer will be enhanced in its flame resistance and the like. If the group contains additional hydroxyl, amino or carboxyl groups, the interpolymer can be inter-reacted with such resinous materials as phenol or urea formaldehyde resins, polyester resins, polyether resins, polyamide resins, polyurethanes and the like in the form of resinous bodies, fibers or films, to provide a strong integrated relationship therewith or to produce a system which can function as an adhesive, binder or coating capable of forming a strong bonding relationship with fibers, films and products formed of such resinous materials.

It will be apparent from the foregoing that we have provided a new and improved compound which finds utility in the manufacture of polymeric materials having novel characteristics.

It will be understood that changes may be made in the details of formulation and operation, without departing from the spirit of the invention, especially as defined in the following claims.

We claim:
1. The compound having the general formula

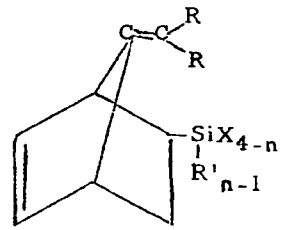

in which R is selected from the group consisting of hydrogen, a lower alkyl group, a halogen substituted lower alkyl group, and an unsaturated aliphatic group, X is a highly hydrolyzable group, and $n$ is a number of from 1 to 3.

2. The compound as claimed in claim 1 in which the R groups attached to the double bond in the 7 position are methyl.

3. The compound as claimed in claim 1 in which X is chlorine and $n$ is 1.

4. The adduct 7-isopropylidenyl-5-trichlorosilyl-2-norbornene.

5. The method of producing the adduct 7-isopropylidenyl-5-trichlorosilyl-2-norbornene comprising reacting dimethyl fulvene with vinyl trichlorosilane.

6. The compound as claimed in claim 1 in which the highly hydrolyzable group is selected from the group consisting of a tertiary amine and a halogen.

* * * * *

UNITED STATES PATENT OFFICE
CERTIFICATE OF CORRECTION

Patent No. 3,994,947　　　　　　　　　Dated November 30, 1976

Inventor(s) William C. Bond, Jr. et al.

It is certified that error appears in the above-identified patent and that said Letters Patent are hereby corrected as shown below:

column 5, line 64, "4-$^{\circ}$" should read "4-20"

column 10, line 38, "968 $^{116-1}$" should read "968 $cm^{1}$"

Signed and Sealed this

Eighth Day of March 1977

[SEAL]

Attest:

RUTH C. MASON
*Attesting Officer*

C. MARSHALL DANN
*Commissioner of Patents and Trademarks*